May 4, 1976
N. BULL
KALANCHOE PLANT
Filed Dec. 20, 1974
Plant Pat. 3,880
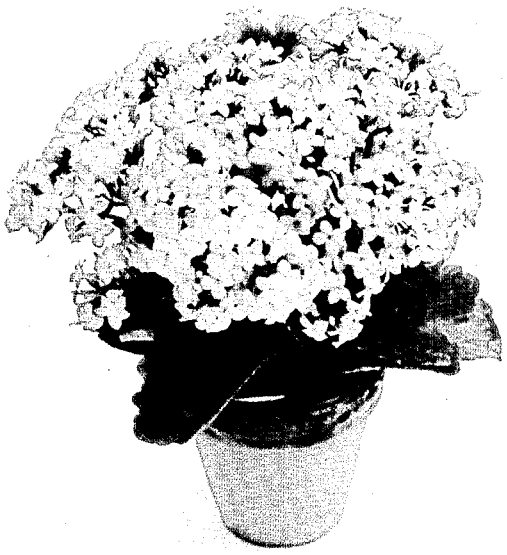

United States Patent

Plant Pat. 3,880

Patented May 4, 1976

3,880

KALANCHOE PLANT

Norbert Bull, Gonnebek, Germany, assignor to Mikkelsens, Inc., Ashtabula, Ohio

Filed Dec. 20, 1974, Ser. No. 535,087

Int. Cl. A01h *5/00*

U.S. Cl. Plt.—68 1 Claim

The present invention relates to a new and distinct variety of Kalanchoe plant known by the varietal name Roter Pfeffer.

The new variety was discovered by me as a selected, cultivated seedling resulting from a cross between B101, the unnamed seed parent, and B103, the unnamed pollen parent. The new cultivar was asexually reproduced by stem cuttings at Gonnebek, West Germany, and the unique characteristics of the new cultivar have been transmitted through successive propagations.

The new cultivar is particularly characterized by its branched out growth habit, abundance of flower stems, relatively large flowers (17 mm.) having a prominent pistil, very good keeping and shipping qualities, and by its strong growth habit which eliminated the need for staking and tieing during early growth stages.

The natural blooming season of the new cultivar is mid to late January, although by steered culturing in the greenhouse, the cultivar can be brought to flowering during the entire year. Flowering response, as controlled by the initiation of short day treatment, is 12 weeks in summer and 14–16 weeks in winter. The time from sticking of cuttings to flowering is 20 or 28 weeks for summer and winter, respectively.

The following description is based on plants of the new cultivar grown in Gonnebek, West Germany, with the plants being grown in 12 cm. pots maturing in mid July. Color references are made to the RHS Colour Chart except where general color terms of ordinary dictionary significance are used.

The accompanying color photographic drawing shows a typical blooming plant of the new cultivar, with the color being as true as possible with color illustrations of this type.

*Parentage:* The new cultivar is a seedling resulting from crossing the seed parent B101, an unnamed and unpatented variety, with the pollen parent B103, also an unnamed and unpatented Kalanchoe variety.

*Propagation:* By asexually propagating stem cuttings, it has been successfully demonstrated that the new cultivar is stable and produces true to type.

(A) *Type cutting:* 15 mm. to 25 mm. long terminal cuttings.

(B) *Time to root:*
10 days at 24° C. summer.
15 days at 20° C. winter.

(C) *Rooting habit:* Typical for commercial cultivars, having a profusion of fibrous dendritic roots. Roter Pfeffer is the fastest rooting of my four Kalanchoe cultivars, with my other Kalanchoe cultivars being disclosed in pending application Ser. Nos. 535,199, filed Dec. 20, 1974 (Cherie); 535,128, filed Dec. 10, 1974 (Korall) and 535,200, filed Dec. 20, 1974 (Granat).

PLANT DESCRIPTION (A) *Form:* short, compact, erect, with excellent self branching. The shortest cultivar with smallest leaves of my comparable cultivars Korall and Cherie, being approximately 20 cm. above the top of the pot when grown as indicated above. Inflorescence gives appearance of being flat.

(B) *Habit of growth:* Slow growing, self branching with excellent vigor to produce strong self supporting stems that measure 6–10 mm. in diameter.

(C) *Foliage:* Small to medium, with above average quantity.

(1) *Size:* Small to medium size for kalanchoes measuring 6 cm. wide by 7–8 cm. long, petiole 5–8 mm. long, leaf base obtuse.

(2) *Shape:* Oval, appearing to be elliptical because of longitudinal cupping along the mid rib.

(3) *Texture:* Slightly rugose, thick, fleshy, coriaceous, underside glabrous.

(4) *Margin:* Crenate, outer end rounded.

(5) *Color:* Young foliage, top side green 137A underside green 138A; mature foliage, top side green 137A to yellow green 147B, underside green 138AB.

FLOWERING DESCRIPTION (A) *Flowering habits:* Flowering is quite uniform with 90% of total buds being in flower at the beginning before the first flowers deteriorate. Flowers have excellent keeping quality and give a fresh appearance for three to four weeks. Petals do not lie flat, thereby showing the reverse side which tends to dilute the overall true color.

(B) *Natural flowering season:* In northern latitudes early to mid January. Flowering time under controlled day-length at 22° C. in summer is 12–13 weeks; in winter is 12–14 weeks. There is some indication of heat delay during summer months.

(C) *Flower buds:* Typical of four petalled corollas and measure 5–6 mm. long and 1.5 to 2 mm. in diameter at the base.

(D) *Flowers borne:* On compound paniculate cymes. The primary peduncles are short compared to Korall and Cherie, measuring approximately 8 to 10 cm.; flower pedicles are 4–5 mm. long.

(E) *Quantity of flowers:* Above average for total plant because of self branching and high number of secondary flowering shoots.

(F) *Petals:* Distinctly separated and borne at approximately 30° angle.

(1) *Shape:* Elliptical, measuring 5 mm. wide x 7–8 mm. long; total flower diameter 17–18 mm.

(2) *Color (summer):* Top side, when opening, red between 43A and 44B, fading to red 41B to 43C; underside, red 48B–C.

(3) *Number of petals:* Generally four, occasionally five, no overlapping.

(G) *Reproductive organs:*

(1) *Stamens:* Eight in number.
(a) anther shape: typical, color: dark brown.
(b) filament color: yellow green, translucent.
(c) pollen color: yellow.

(2) *Pistils:*
(a) stigma shape: flat rounded color, crystalline white.
(b) style color: light green translucent.
(c) ovaries: four in number, 2–3 mm., color green.

DISEASE RESISTANCE

Does not become infected with mildew when grown with cultivars susceptible and infected with that disease.

I claim:

1. A new and distinct variety of kalanchoe characterized particularly by its excellent self-branching, numerous umbels on strong stems, relatively large red flowers, strong growth habit, and by its excellent keeping and shipping qualities.

No references cited.

ROBERT E. BAGWILL, Primary Examiner